United States Patent
Chen et al.

[19]

[11] Patent Number: 5,907,291
[45] Date of Patent: May 25, 1999

[54] MULTI-PATIENT MONITORING APPARATUS AND METHOD

[75] Inventors: Yunquan Chen, Vancouver; Steven Howard Hill, Nanaimo, both of Canada; Antonio Hines, Tampa, Fla.; Cecil Hershler, Vancouver, Canada

[73] Assignee: VSM Technology Inc., Vancouver, Canada

[21] Appl. No.: 08/870,069

[22] Filed: Jun. 5, 1997

[51] Int. Cl.[6] .................................................. G08B 21/00
[52] U.S. Cl. .................. 340/870.16; 340/573; 600/484; 600/509; 600/300
[58] Field of Search .............................. 340/573, 870.16, 340/870.17; 128/710, 696; 600/459, 484, 486, 490, 300, 509, 301

[56] References Cited

U.S. PATENT DOCUMENTS

| | | | |
|---|---|---|---|
| 4,958,645 | 9/1990 | Cadell et al. .............................. | 600/484 |
| 4,981,139 | 1/1991 | Pfohl ........................................ | 600/484 |
| 5,157,604 | 10/1992 | Axford et al. ............................ | 600/508 |
| 5,163,380 | 11/1992 | Duffy et al. .............................. | 119/418 |
| 5,253,648 | 10/1993 | Walloch ................................... | 600/494 |
| 5,262,944 | 11/1993 | Weisner et al. .......................... | 600/300 |
| 5,309,920 | 5/1994 | Gallant et al. ........................... | 600/523 |
| 5,337,751 | 8/1994 | Newell et al. ............................ | 600/459 |
| 5,355,890 | 10/1994 | Aguirre et al. ........................... | 600/493 |
| 5,417,222 | 5/1995 | Dempsey et al. ........................ | 600/509 |
| 5,421,341 | 6/1995 | Marangoni ............................... | 600/490 |
| 5,427,109 | 6/1995 | Frankenreiter .......................... | 600/493 |
| 5,458,123 | 10/1995 | Unger ....................................... | 600/509 |
| 5,482,049 | 1/1996 | Addiss et al. ............................ | 600/486 |

*Primary Examiner*—Michael Horabik
*Assistant Examiner*—Albert K. Wong
*Attorney, Agent, or Firm*—Shlesinger, Arkwright & Garvey

[57] ABSTRACT

An apparatus and method for monitoring conditions of living beings. A telemetry device includes a monitor which monitors at least one physiological condition of a patient. A transmitter transmits data including information on the condition and information identifying the device or patient. A separate receiver is provided for each device to receive the data transmitted. The receiver outputs signals to a processor. The processor extracts the information on the physiological condition and the information identifying the telemetry device. The processor outputs the information in a digital form to a display unit. The display unit displays the information on the physiological condition and the identifying information in a readable form. There is a separate display area for each telemetry device, whereby a plurality of patients can be monitored simultaneously on a real time or a near real time basis.

23 Claims, 7 Drawing Sheets

MULTI-PATIENT MONITORING APPARATUS AND METHOD

BACKGROUND OF THE INVENTION

This invention relates to apparatuses and methods for monitoring physiological conditions and, in particular, devices and methods suited for monitoring a plurality of ambulatory patients simultaneously from a remote location.

Physiological conditions of patients, such as blood pressure and heart rate, have been conventionally monitored using one monitor per patient. The equipment is linked to the patient and thereby restricts his or her movement. The monitoring is usually done in the presence of healthcare professional and the procedure itself can affect the physiological conditions (also known as vital signs) being monitored.

There has been an increased need to provide an apparatus and method for monitoring a plurality of patients simultaneously and automatically without restricting movement of the patients concerned and without requiring the presence of healthcare providers. A number of automated, ambulatory systems have been developed for blood pressure measurement for example. However, typically the patient must report to a medical office or other specified location in order to download the information collected. Real time or near real time information about an ambulatory patient is not conventionally available. Such a system would be desirable and would reduce the costs of monitoring a plurality of patients.

U.S. Pat. No. 4,958,645 to Cadell discloses a medical radio telemetry system which includes a plurality of telemeters with one telemeter located on each patient. The patent also discloses a method of switching antennas to obtain the best signal. However there is no provision for automatically identifying and displaying the different signs of a plurality of patients separately on a remote computer. Furthermore, utilizing a plurality of antennas may not increase the reliability of the system when both antennas encounter the same random noise simultaneously.

U.S. Pat. No. 5,482,049 to Addiss et al. discloses a method for labelling various vital signs of a patient. However the system is not well adapted for simultaneous use on a plurality of patients.

U.S. Pat. No. 5,157,604 to Axford et al. discloses a method for monitoring heart rate for plural persons using radio telemetry. The system however uses pre-determined time sequences. This means time is wasted in sending data from patients when monitoring is not required. A preferable system would transmit data on demand.

U.S. Pat. No. 5,417,222 to Dempsey et al. discloses a method and apparatus for performing patient monitoring which interfaces a telemetry monitor with a standard portable computer. The system however does not have adequate provision for separately monitoring a plurality of patients.

Accordingly, it is an object of the invention to provide an improved telemetry monitoring system which can simultaneously display physiological conditions of a plurality of patients on a real time or near real time basis.

It is also an object of the invention to provide an improved telemetry monitoring system which is compatible with standard desktop computers commonly used in medical facilities.

It is a further object of the invention to provide an improved telemetry monitoring system which is reliable and relatively error-free.

It is a still further object of the invention to provide an improved telemetry monitoring system which is efficient and, in particular, transmits information at a rate or at times dictated by demand.

SUMMARY OF THE INVENTION

In accordance with these objects, there is provided an apparatus for monitoring conditions of living beings. The apparatus includes a telemetry device with a monitor for monitoring a physiological condition and a transmitter operatively connected to the monitor which transmits a signal carrying information on the condition and identifying information on the device. There is also a receiver capable of receiving the signals transmitted by the telemetry device and which outputs the received data. There is a processor operatively connected to the receiver which extracts the information on the physiological condition from the output data, integrates it with the identifying information, and outputs the information on the condition and the identifying information in a data package. A central processing unit is operatively connected to the processor and dispatches the information on the physiological condition according to the identifying information. A display unit is operatively connected to the processor and displays the information on the condition and the identifying information in a readable form.

Preferably the apparatus includes a plurality of telemetry devices, each said device having unique identifying information.

Each such identifying information may be a frequency at which each said telemetry device operates.

Preferably there is a separate receiver for each said device.

The display may have a separate area for each said device. Each area displays identifying information and information on the physiological condition monitored by each said device.

Alternatively there may be a display area shared by the devices.

The information may be transmitted by each telemetry device in binary sequences. Each sequence includes indicia identifying the type of message and parameters representing the physiological condition. At least some of the messages include information on an operating state of one of said monitors.

Preferably the data processing unit and display are components of a desktop computer system.

The invention addresses a number of problems encountered with previous devices and meets a long standing demand for such equipment.

In particular, a plurality of patients can be fitted with separate telemetry monitoring devices for monitoring such physiological conditions as blood pressure and heart rate. The patients are relatively unrestricted in their movements within certain limits such as a hospital ward or floor. Signals from the monitoring devices are transmitted to a remote station, such as a personal computer, where the conditions of a plurality of patients can be displayed simultaneously to a single health professional. The data can be transmitted at a rate dependent upon the state of operation of the monitoring device. For example, relatively infrequent transmissions are required between blood pressure measurements. However, the monitoring device may become active periodically by, for example, pressurizing a blood pressure cuff in order to measure blood pressure. When this active mode of operation occurs, the rate of transmission can increase.

In addition, the transmissions can be encoded with information to identify the particular monitoring device and accordingly the patient wearing the particular device. This information can be decoded by the processor and displayed simultaneously with the physiological conditions.

DESCRIPTION OF THE PREFERRED EMBODIMENTS

Figure 1:
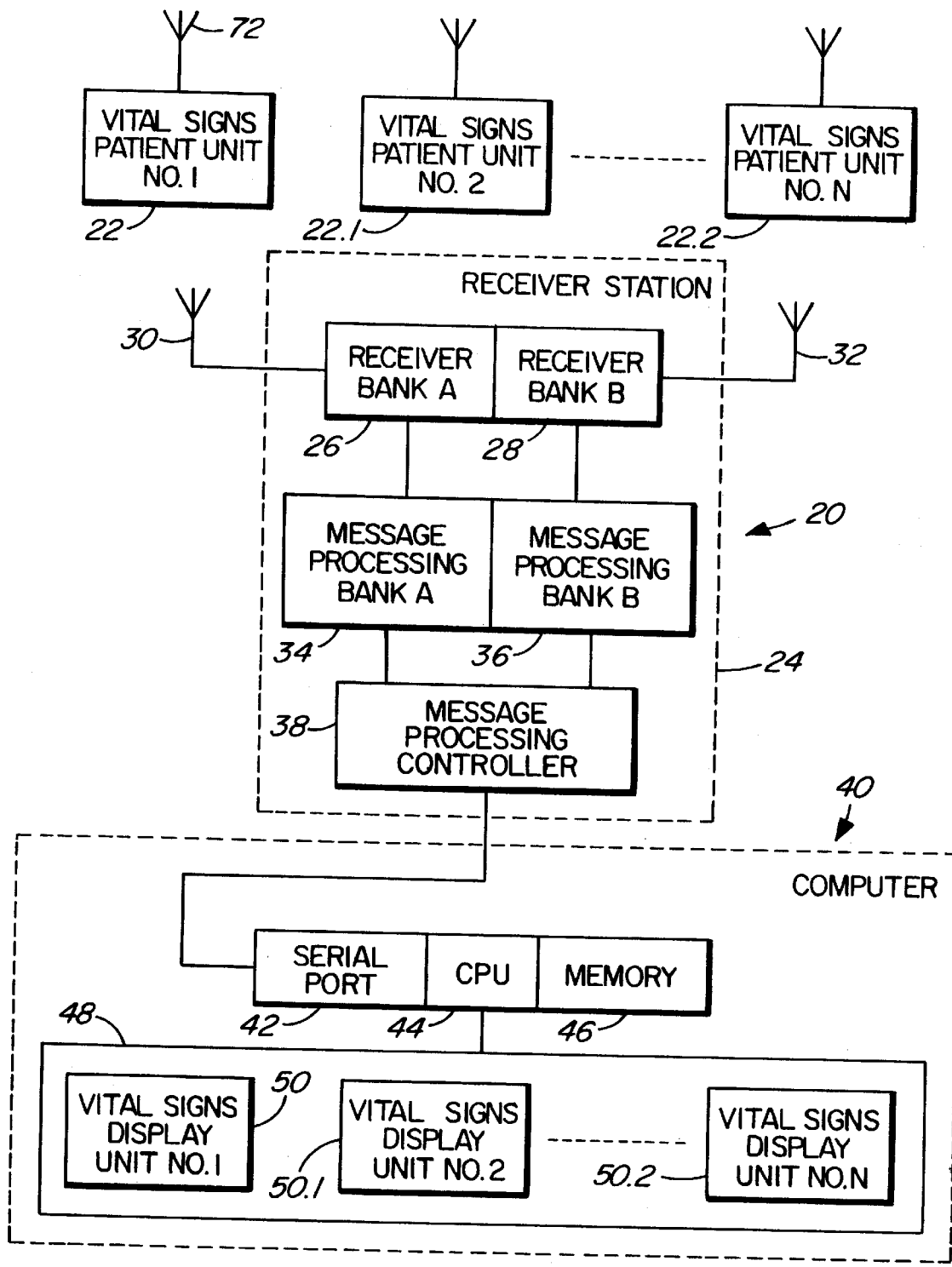
FIG. 1 is a block diagram of an apparatus for monitoring conditions of living beings, according to an embodiment of the invention.

Referring to the drawings, FIG. 1 shows an apparatus and method 20 for monitoring biological signals according to an embodiment of the invention. The apparatus includes three types of components. There is at least one telemetry device including a monitor for monitoring a physiological condition of a living being, typically a human patient, and a transmitter for transmitting information on this condition. Usually however a plurality of such devices would be utilized and two additional devices 22.1 and 22.2 are illustrated in FIG. 1. One of these devices is typically used for each patient or other living being. There is also a receiver station 24 which receives signals transmitted by the devices 22, 22.1 and 22.2. The receiver station in this preferred embodiment includes separate receivers for each of the monitoring devices. Typically the monitoring devices transmit at a characteristic frequency and a separate receiver is provided for each such frequency or bandwidth. The receivers are grouped into a receiver bank. In this example there are two such banks 26 and 28 which are tuned to the same frequency as monitoring devices 22, 22.1 and 22.2. Accordingly there is a pair of receivers, one in bank 26 and one in bank 28, for each monitoring device. Similar paired receivers would be provided for the other devices 22.1 and 22.22. Each receiver bank is connected to a separate antenna 30 and 32 in this example.

The receivers are connected to separate message processing units in two banks 34 and 36 which in turn are connected to a message processing controller 38.

The receiver station is connected to a computer 40 which is typically a standard desktop computer. Alternatively specialized processing and display units could be utilized.

The receiver station 20 is connected to the computer in this example through serial port 42. The computer also includes a central processing unit 44 and a memory 46 in the conventional manner. The term "computer" or "computer system" also includes a conventional video display unit 48. A separate area of the screen is provided for each of the monitoring devices 20, 22 and 22.1. Alternatively the same area of the screen could be used for each device but showing each device at different times. In this example, areas 50, 50.1 and 50.2 are provided for the devices 22 and 22.1 and 22.2 respectively. Preferably these are shown simultaneously in separate areas of the screen. Possibly however only a fraction of the total number of monitoring devices can be shown on the screen at one time if there are a large number of patients being monitored simultaneously.

Figure 2:
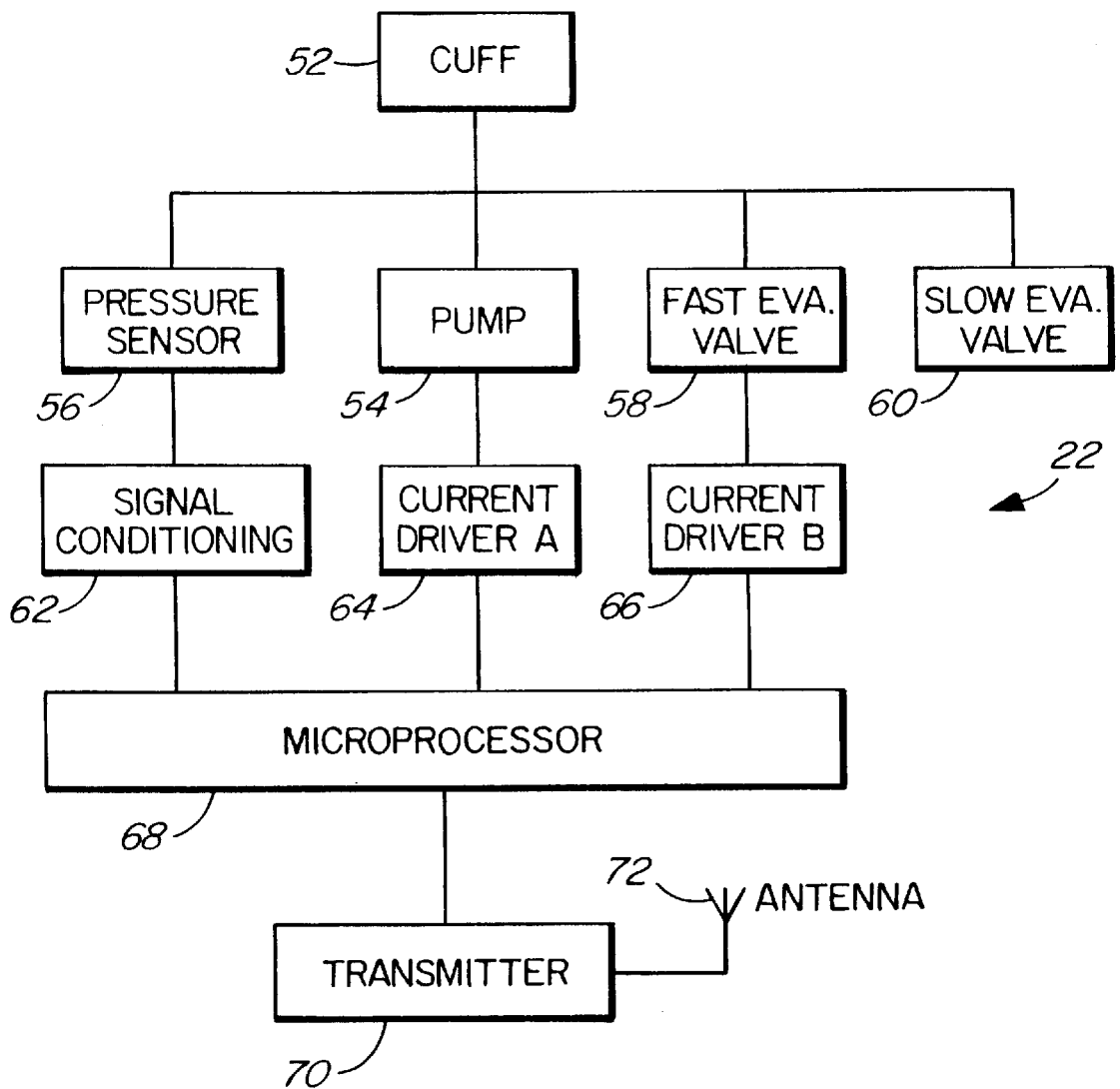
FIG. 2 is a block diagram of a telemetry device for the apparatus of FIG. 1.

Referring to FIG. 2, this shows details of telemetry device 22. In this example, the physiological conditions monitored include blood pressure and heart rate. The device includes a blood pressure cuff 52 for occluding blood vessels of a patient. The device also has an air pressure pump 54 for pressuring cuff 52. A pressure sensor 56 monitors pressure in the cuff. There is a fast evacuation valve 58 for rapidly decreasing the internal pressure of the cuff. This valve is opened during an initialization process prior to each measurement being taken. It is also used after the measurement is completed. There is also a small, fixed aperture for slowly decreasing the pressure while the measurement is being taken.

Two electrical current drivers 64 and 66 provide electrical current for running the pump 54 and fast evacuation valve 56 respectively. A microprocessor 68 controls the operation of the device 22 and prepares data for transmission. An RF transmitter 70 transmits data to receiver station 24, shown, in FIG. 1, via antenna 72.

In the preferred example, the components shown in FIG. 2, apart from cuff 52, are built into a bag. A hook portion of a hook and loop-type fastener is sewn onto the bag.

Cuff 52 has an internal bladder with a length of air tubing connecting it to pressure sensor 56, pump 54 and ale valves 58 and 60 a via multi-terminal tube connector. Die loop portion of the fastener is sewn onto the cuff. After the cuff has been applied to the limb of a patient, the bag is attached to the cuff by means of the hook and loop-type fastener.

Blood pressure is calculated by means of oscillometry. Signal conditioning circuitry 62 has a band pass filtering circuit (0.5 Hz to 5 Hz) which extracts oscillations from the cuff signal provided, by pressure sensor 56. The signal conditioning circuitry 62 has another low pass filtering circuit (0 to 0.5 Hz) which smooths the steady cuff pressure signal. Both the oscillation pressure signal and steady pressure signal are amplified by the circuitry 62 to provide adequate signal levels to microprocessor 68.

The current drivers 64 and 66 are transistor circuits which provide large currents for pump 54 and fast evacuation valve 58 when they receive command signals from microprocessor 68. The microprocessor also executes an analysis algorithm on the oscillation and steady cuff pressure signals from the signal conditioning circuitry 62 and codes of the data to be sent to transmitter 70.

Figure 3:
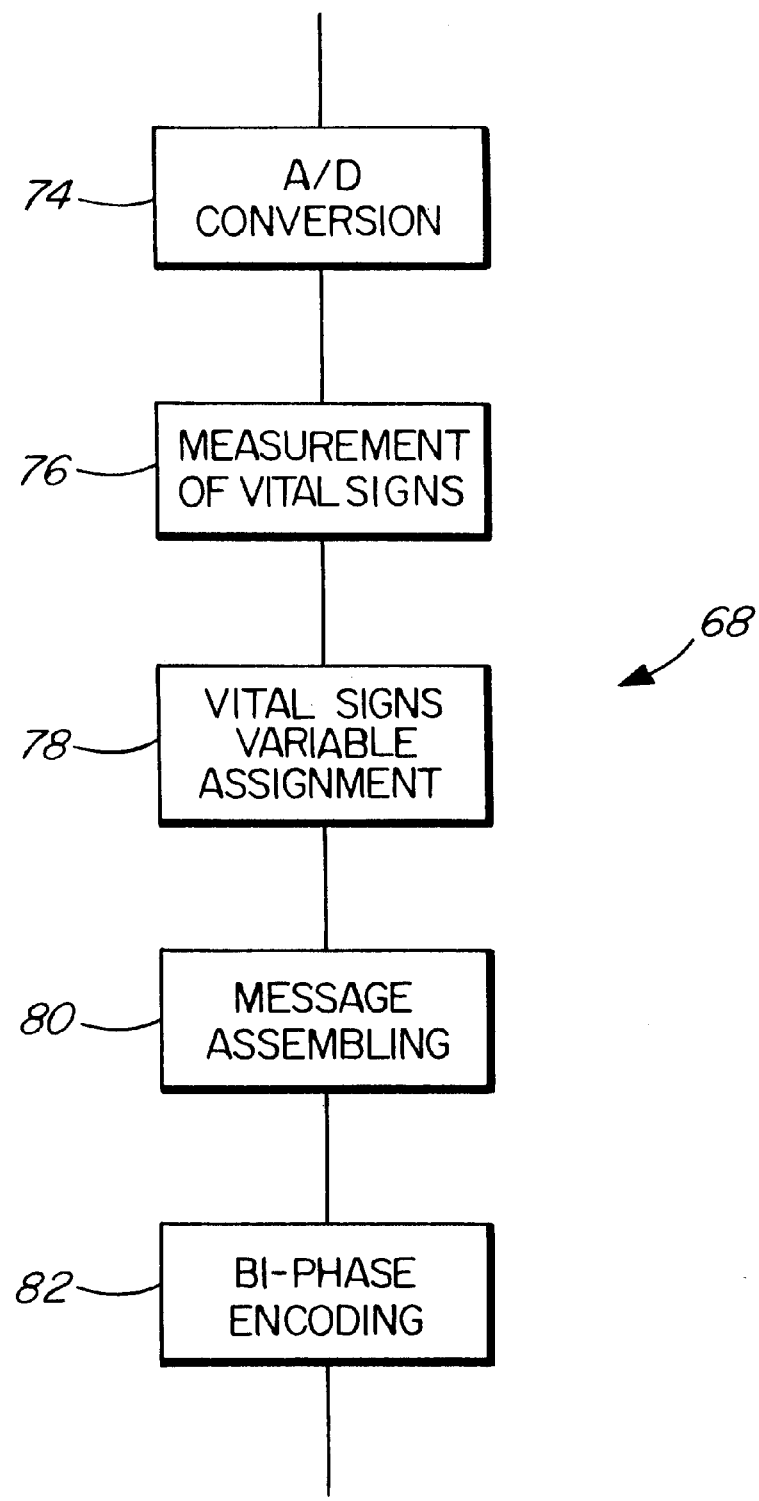
FIG. 3 is a block diagram displaying the operations of the processor used in the telemetry device of FIG. 2.

FIG. 3 illustrates the core operations of microprocessor 68. Oscillation and steady cuff pressure signals are acquired through analog/digital conversion function 74. The oscillation signals are sampled at 12–36 points per second and the steady cuff pressure signals are sampled at 3–9 points per second in the preferred embodiment. These rates can be changed in alternative examples of the invention. After the data are collected, calculations of systolic, diastolic and heart rate are carried out in the measurement of vital signs operation 76.

Vital signs variables to be transmitted are assigned to different message types and parameters in the vital signs variable assignment operation 78. This is done according to the mode of operation of the telemetry device. The device starts with a waiting state after the device is turned on. This is followed by an occluding state in which the cuff is pressurized. This is followed by a measuring state in which the cuff is slowly de-pressurized and oscillations are monitored. Lastly there is a completed state in which the measurement results are determined and the cuff is rapidly de-pressurized.

There are six message types used for the four modes of operation described above. These are numbered 1–6 in Table I. Type 1 messages are sent at a very low rate, about one message every three seconds in this particular example. Type 2 messages are sent at a slightly higher rate of about one message per second. Types 3 and 4 messages are sent alternatively at a rate of between three and nine messages per type per second. There are four samples of the oscillation signal and one sample of the steady cuff pressure signal provided in each of the two messages of types 3 and 4 respectively. Accordingly the oscillation signal is sampled at a frequency four times that of the steady cuff pressure signal. Accordingly, a sampling rate of 3–9 points per second is achieved for steady cuff pressure and 12–36 points per second for the oscillation signal when the messages are sent alternatively at the rates of three and nine messages per type per second. Type 5 messages are sent one per second. Type 6 messages are sent once per measurement cycle. Each measurement is sent in duplicate for reliability. These figures may vary for other embodiments of the invention.

In all four states of operation, the cuff pressure is continuously monitored for safety reasons. Each message includes information on three parameters P1, P2 and P3. These three parameters vary according to the message type. There are time-out counters provided via parameter P3 in all three pressurized states. When the cuff pressure exceeds a certain value set for each of the four states, or the elapsed time exceeds a pre-set limit, the fast evacuation valve 58 is opened to provide immediate assistance for the patient.

The waiting, state can be programmed to extend for any length of time. Typical choices are 5, 10 or 30 minutes. During the waiting state, the count-down waiting time is continuously monitored via parameters P2 and P3 which include the high byte and low byte of the wait times respectively. This allows prediction of the next measurement times by a healthcare worker. Each of the parameters P1, P2 and P3 is eight bits long. Accordingly two parameters P2 and P3 can provide a waiting time withing the range of 0–65535 seconds or 0–18.2 hours. The average data rate for a patient is low during this time, permitting a large number of telemetry devices to operate simultaneously in the system.

The occluding state starts at the end of the waiting state. At this time the cuff pressure is pumped quickly via pump 54 to a pressure which can be pre-determined or determined during the pressurizing process. After the cuff pressure reaches that value, the measuring state begins and both the cuff pressure and oscillation signals are transmitted. The oscillation signal is not usually required because the systolic, diastolic and heart rate values are determined in the measurement of vital signs operation 76 shown in FIG. 3. However, if those values appear suspicious then the raw oscillation signal combined with the raw cuff pressure signal provide a means for further evaluation of the obtained data and/or the performance of the system.

The last mode of operation of the system is the completed state. During this mode of operation, the microprocessor makes sure that the fast evacuation valve is open and the cuff pressure drops quickly to close to atmospheric pressure before beginning another waiting state.

Referring back to FIG. 3, after the assignment of vital signs variables to a particular message type and its parameters, the message type and parameters are assembled into a message in message assembling operation 80. All messages are formatted the same. Each message from the telemetry device in this example is 5 bytes long starting with a Header byte followed by the least significant 7 bits of the three parameters. The message is ended with a check sum byte. The Header byte is identified by the set (1) of bit 7 plus the clear (0) of bit 0. All others have a cleared (0) bit 7. In the Header byte, 3 bits B6, B5 and B4 are used to represent message types 1–6 . For example, 000 represents message type 1, 001 represents message type 2 and 010 represents message type 3. Bytes B3, B2 and B1 of the Header bytes are the most significant bits B7's of the Parameters P1, P2and P3respectively.

Each bit of the check sum byte except for the most significant bit B7 is the logic sum of the corresponding bits of all of the Header and Parameter bytes. This check sum byte is used for the detection of transmission error in the receiving station 24 shown in FIG. 1.

Referring again to FIG. 3, after the vital signs variables are assigned to message parameters of a message type and the message is assembled, the message is converted in a bi-phase encoding operation 82 to a standard bi-phase digital signal to be fed to the transmitter 70 shown in FIG. 2. Bi-phase digital format is preferred to avoid unbalanced "0's" and "1's" in the transmitted data.

The message provided by the microprocessor 68 is modulated in amplitude modulation (AM) by transmitter 70 and sent out as an RF signal via antenna 72. Each message is sent twice to increase the reliability of the system. Two idle bytes (Hexadecimal FF) are sent between different messages, but not between two transmissions of the same message, to separate messages and to synchronize the message transmission and receiving process.

Referring back to FIG. 1, the RF signals sent by the telemetry units 22, 22.1 and 22.2 are received by receiver banks 26 and 28 of receiver station 24 via antennas 30 and 32. Each receiver bank has one and only one RF receiver which matches in frequency the RF transmitter of one of the telemetry units 22, 22.1 or 22.2. In other words, the number of receivers in each of the receiver banks 26 and 28 is equal to the number of telemetry devices. Each telemetry device and the corresponding receiver in each of the two receiver banks has the unique frequency so that there is no cross-talk between different telemetry units. Antennas 30 and 32 are spaced-apart such that poor transmission is less likely to happen in both receiver banks.

Receiver banks 26 and 28 demodulate the received signals into their original bi-phase digital format and feed the bi-phase digital signals to the message processing banks 34 and 36 respectively. These banks have a processing unit for each receiver in each of the receiving banks. Each processing unit is connected to one receiver only. In this way, each telemetry device is associated with a unique receiver and each receiver is associated with a unique processing unit.

Figure 4:
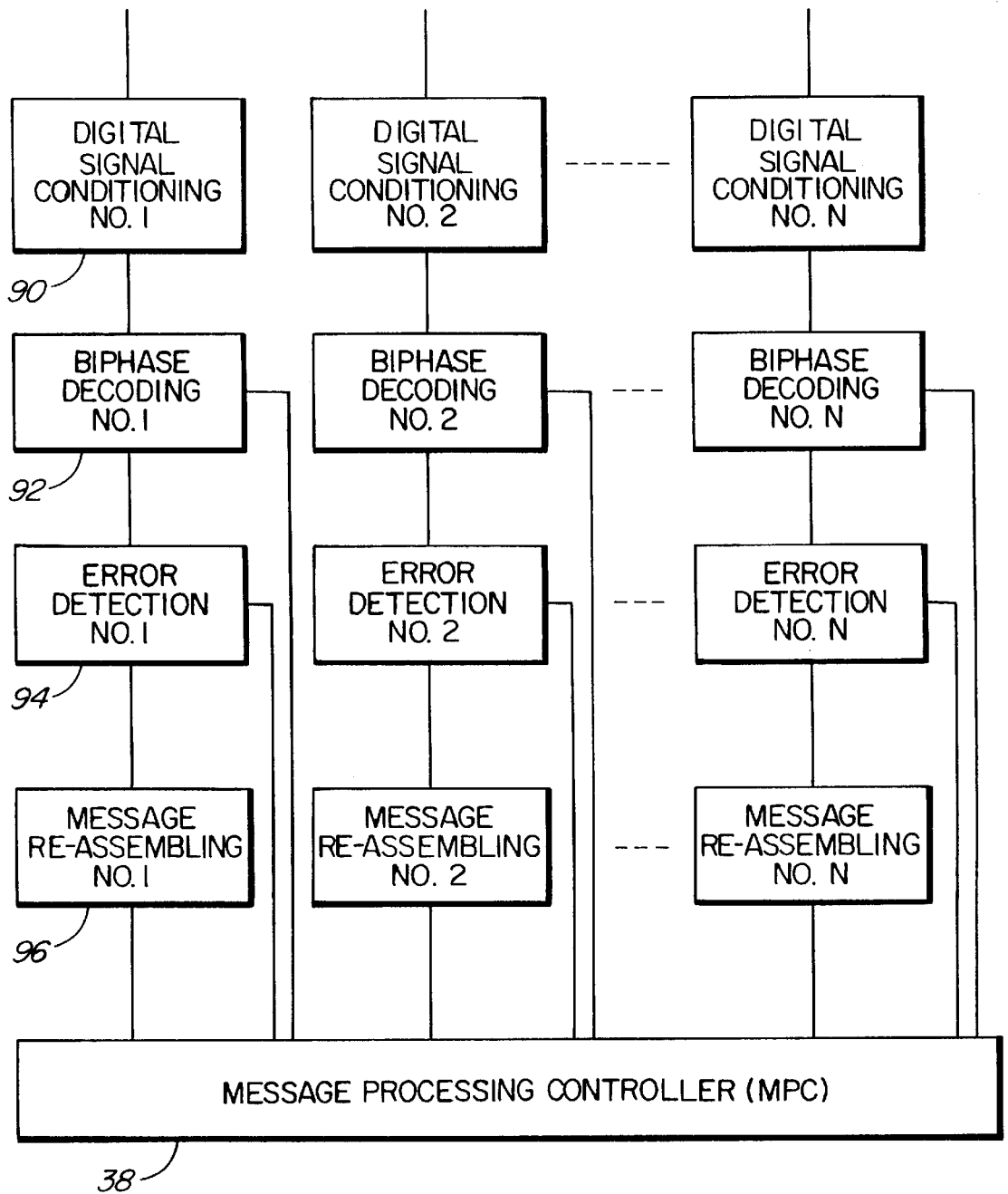
FIG. 4 is a block diagram of one of the message processing banks and the message processing controller in the receiving station of the apparatus shown in FIG. 1.

FIG. 4 shows the operations performed in message processing banks 34 and 36 in association with message processing controller 38 shown in FIG. 1. Each bi-phase signal is first conditioned in a digital signal conditioning operation 90 to remove noise and amplitude variations and form a standard TTL (transistor-transistor logic) signal. The conditioned bi-phase signal is next converted in bi-phase decoding operation 92 into a standard non-return-to-zero (NRZ) signal. The message is then fed to an error detection operation 94. The logical sum of the same bits, B6–B0 of all of the Header and data bytes is calculated and compared to the corresponding bit of the Check sum byte. If any discrepancy occurs, a transmission error is found and the transmission is marked as invalid. Otherwise it is presumed valid.

The reassembling operation discards the check sum byte of the original message and inserts a new byte. The newly added byte is a patient unit identification byte which characterizes the particular telemetry device as determined by the frequency of its signal, and accordingly the particular receiver in each receiver bank and particular message processing unit in each message processing bank which produces the message. As with the data bytes, the most significant bit b7 of the patient unit byte is held in the Header byte B0 and B7 of the telemetry device byte is cleared ("0") all of the time. This allows up to 256 telemetry devices to be utilized by the system.

Message processing controller 38, shown in FIG. 1 and 4, coordinates all of the digital processing operations of all of the message processing units in the banks 34 and 36. Three such message processing units are shown in FIG. 4. The controller 38 stops, starts or resets digital operations 90–96 upon request from the computer 40 shown in FIG. 1. The controller 38 also collects messages from either message processing bank 34 or 36. All of the processing units are scanned in order, first starting with a unit in bank 34 and then the corresponding unit in bank 36. If bank 34 has a flag set indicating a valid message, then the controller collects the message and does not collect the message in bank 36. If there is no valid message in bank 34, then bank 36 is checked for a valid message. All valid messages are collected by the controller 38 and sent over serial port 42 to the computer 40 as shown in FIG. 1.

Figure 5:
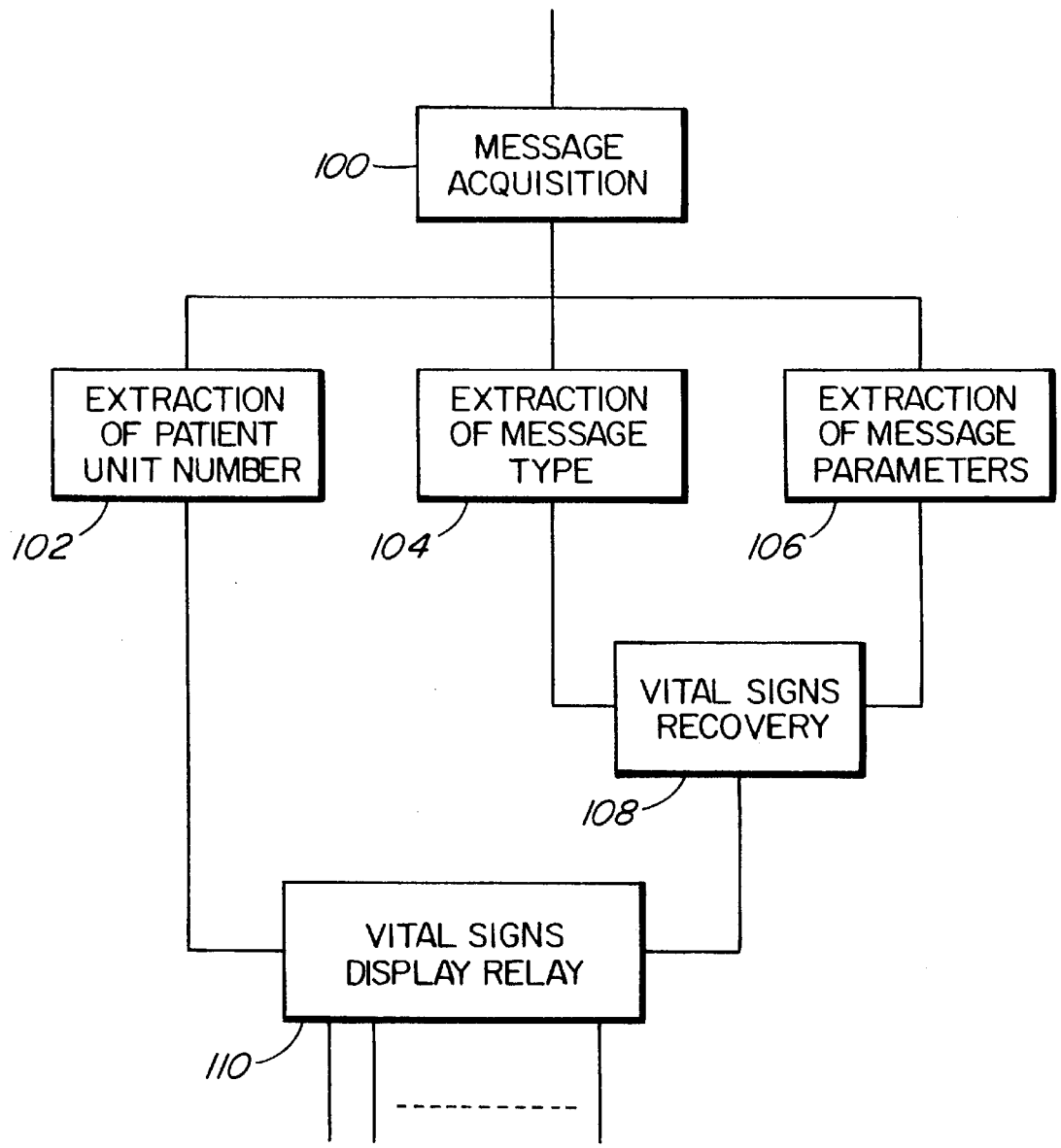
FIG. 5 is a block diagram of the data acquisition and display software for the computer of the apparatus of FIG. 1.
Figure 6A:
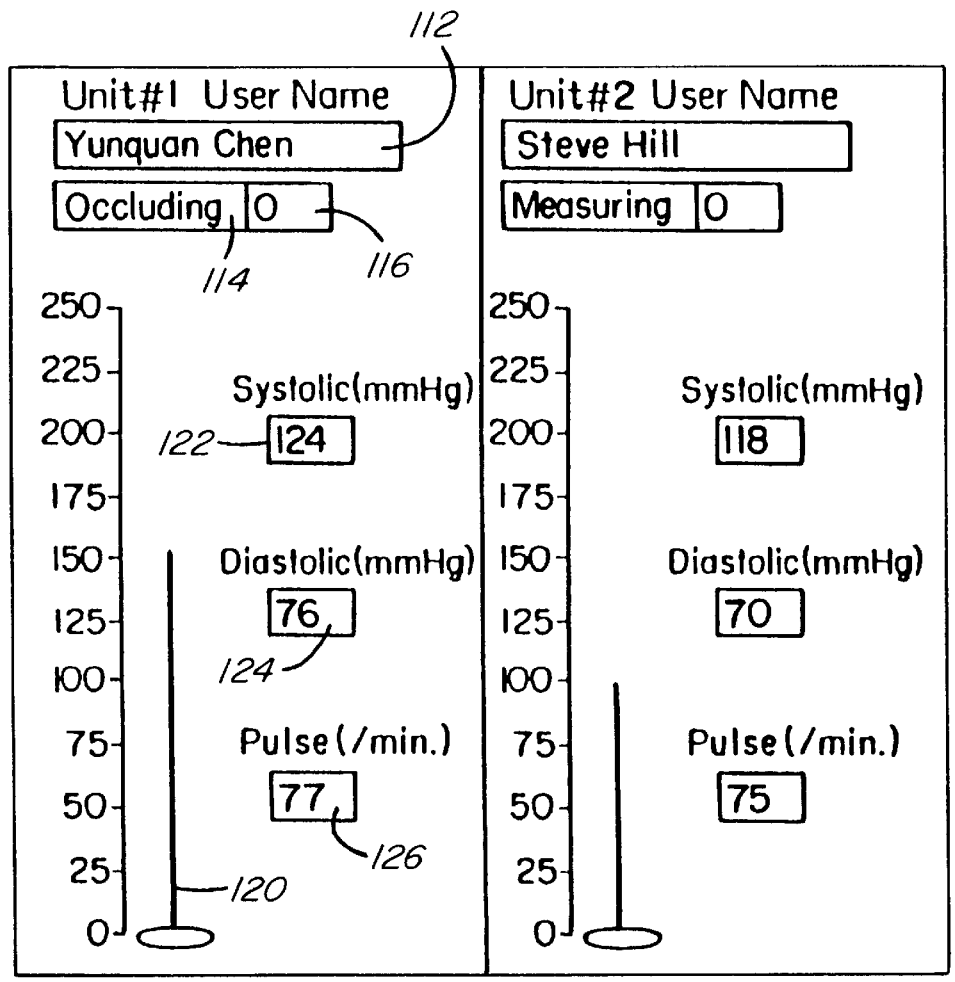
FIG. 6 is a diagrammatic view of the display utilized by the computer in the apparatus of FIG. 1.
Figure 6A:
Figure 6A:
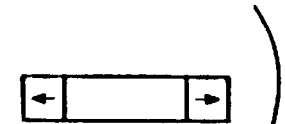
Figure 6B:
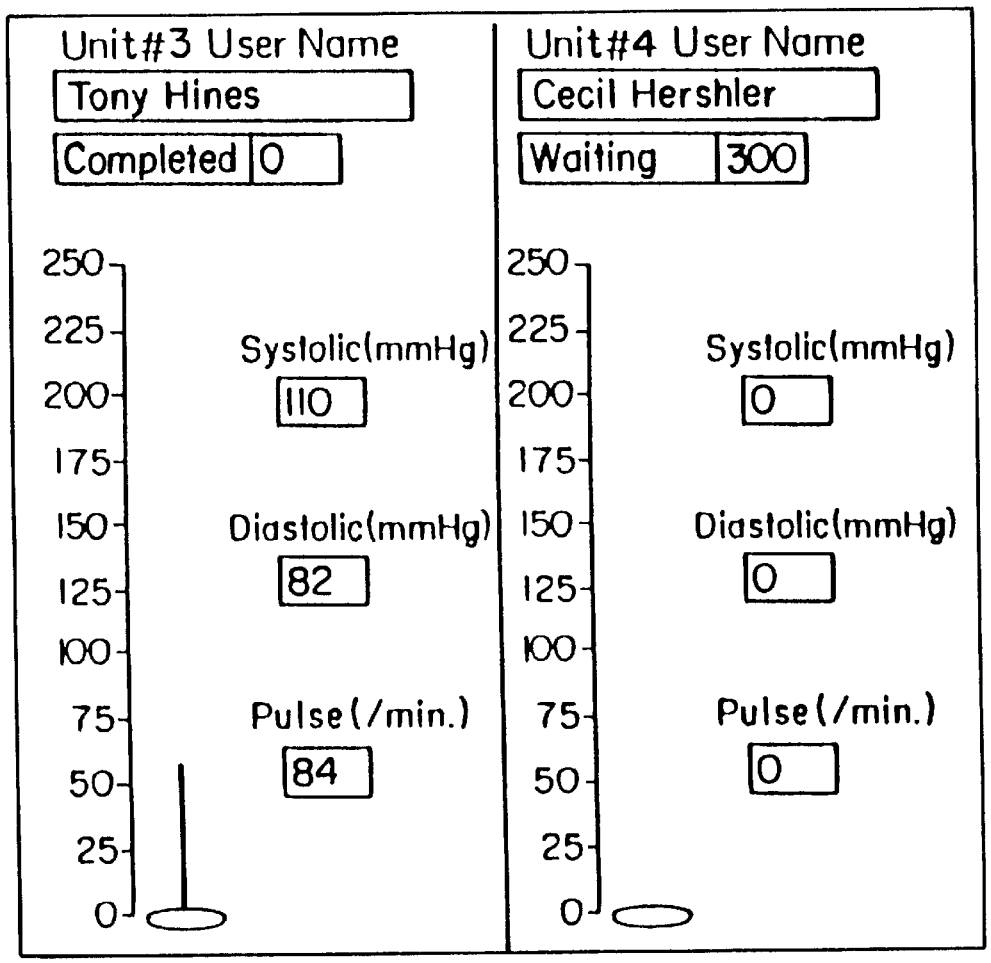
Figure 6B:
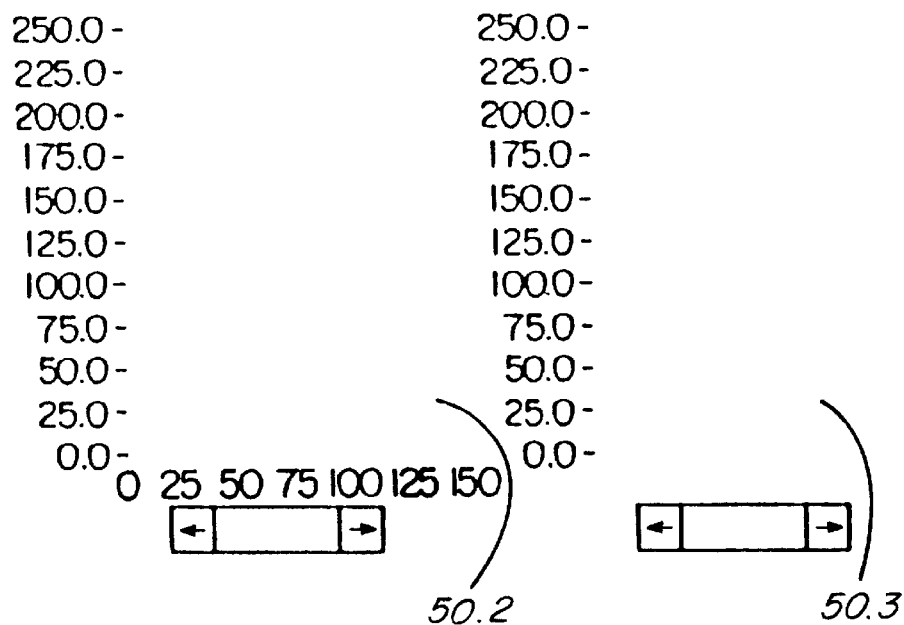

FIG. 5 shows the message acquisition and processing operations in the cpu 44. Message acquisition operation 100 is a one-time initialization process which is executed at the start of a program. This initializes the serial port 42 of the computer. A reset command is then sent to controller 38. After that a command for data transmission is sent. After the initialization process is completed, repetitive message acquisition and processing begins. Five bytes of data are first acquired. Bit 7 of each byte is tested to search for the Header byte characterized by "1". If a Header byte is found then a message of five consecutive bytes will be formed starting with the Header byte. If the Header byte is not found, then more bytes are acquired until the Header byte is found and the message of five consecutive bytes comprising a Header byte and the consecutive four bytes is formed. Such a message is sent to the following processing operations. Acquisition of messages as well as the following processing operations are repeated until the program is stopped by an operator.

There are three subsequent operations shown in FIG. 5 including extraction of patient unit number 102, extraction of message type 104 and extraction of message parameters 106. After the message type and parameters are ascertained, the vital signs variables are recovered in vital signs recovery operation 108. The vital signs variables obtained are then relayed to refresh one of the display units 50, 50.1. and 50.2 shown in FIG. 1 according to the patient unit number. Each display unit bears the identity of the particular telemetry device providing the information displayed. For example, display 50 shows the number 1 which corresponds to the number 1 on telemetry device 22. This is done in vital signs display relay operation 110.

FIG. 6 shows the three vital signs display units 50, 50.1 and 50.2 of FIG. 1 plus an additional such unit 50.3. Each display unit in this example indicates the name of the patient in field 112. Each display unit appears as a front panel as an independent instrument or as multiple modules of an instrument. More display units can be seen, if more patients are being monitored, by moving the computer screen window with a mouse or a computer keyboard.

Field 114 under the patient's name indicates the mode of operation of the telemetry device, whether waiting, occluding, measuring or completed. Field 116 to the right is the waiting time or time-out, in seconds.

Cuff pressure is displayed via a simulated mercury indicator 120, while systolic pressure, diastolic pressure and pulse rate are displayed in fields 122, 124 and 126 respectively. These are according to the latest "completed" state.

Below the mercury meter simulation is a chart 130 presenting historic values of the systolic and diastolic pressures obtained in many measurements of the same patient.

It will be understood by someone skilled in the art that many of the details provided above are by way of example only and are not intended to limit the scope of the invention which is to be interpreted with reference to the following claims.

What is claimed is:

1. An apparatus for monitoring conditions of living beings, comprising:

a plurality of telemetry devices, each including a monitor for monitoring a physiological condition and a transmitter operatively connected to the monitor which transmits a unique signal carrying information on the condition and identifying information on each said device;

a plurality of receivers, each capable of receiving the signal transmitted by one said telemetry device only and which outputs received data;

a means operatively connected to the receivers which sequentially acquires the data from the receivers, extracts the information on the physiological condition from the received data, integrates it with the identifying information from the output signals and outputs said information on the condition and the identifying information in a given data format;

a data processing unit operatively connected to the mean operatively connected to the receivers which processes the information and dispatches the information on the physiological condition according to the identifying information; and a display wilt operatively connected to the data processing unit, which displays the information on the condition according to the identifying information in a readable form.

2. An apparatus as claimed in claim 1, wherein the display includes an area shared by a plurality of said devices.

3. An apparatus as claimed in claim 1, wherein the display has a separate area for each of said devices, each said area displaying said identifying information and said information on the physiological condition.

4. An apparatus as claimed in claim 1, wherein each said transmitter is an RF transmitter.

5. An apparatus as claimed in claim 1, wherein the information is transmitted in digital sequences, each said sequence including indicia identifying a type of message and parameters representing the physiological condition.

6. An apparatus as claimed in claim 5, wherein at least some of said messages include information on an operating state of said monitor.

7. An apparatus as claimed in claim 5, wherein each said telemetry device has a processor which outputs parameters representing different physiological conditions, at least some of the messages including a plurality of said parameters representing different physiological conditions.

8. An apparatus as claimed in claim 7, wherein each of the devices transmits data in table form.

9. An apparatus as claimed in claim 8, wherein the data is transmitted line by line according to the table.

10. An apparatus as claimed in claim 7, wherein the monitor is a blood pressure monitor.

11. An apparatus as claimed in claim 10, wherein the monitor includes a blood pressure cuff, an air pump connected to the cuff, a pressure sensor for monitoring pressure in the cuff, a rapid evacuation valve connected to the cuff and a slow evacuation valve connected to the cuff.

12. An apparatus as claimed in claim 11, including a signal conditioner which extracts oscillations from the pressure sensor and outputs oscillation signals and steady cuff pressure signals to the processor.

13. An apparatus as claimed in claim 12, wherein the processor calculates systolic pressure, diastolic pressure and heart rate from the oscillation signals and steady cuff pressure signals.

14. An apparatus as claimed in claim 1, wherein the transmitter transmits a bi-phase digital signal.

15. An apparatus as claimed in claim 14, wherein the transmitter is an amplitude modulation RF transmitter.

16. An apparatus as claimed in claim 1, wherein the data processing unit and the display unit are components of a desk-top computer system.

17. A method of monitoring biological signals, comprising the steps of:

placing a plurality of ambulatory telemetry devices on a plurality of living being;

transmitting RF signals from each of the devices including information on at least one physiological condition of each said being and information uniquely identifying each said device;

receiving the signals of each said device with a separate RF receiver;

sequentially acquiring the data from the receivers and outputting a signal to a processor;

processing information from each said receiver with the processor;

outputting digital signals containing information from each said telemetry device on at least one physiological condition coupled with said information identifying said each telemetry device; and displaying said information, from each said telemetry device on said at least one physiological condition coupled with said information identifying said each telemetry device on a video display.

18. A method as claimed in claim 17, wherein the information from each said telemetry device is displayed in a separate area on the video display.

19. A method as claimed in claim 17, wherein the information from each said telemetry device is displayed in a common area of the display but at different times.

20. A apparatus for monitoring biological signals, comprising:

a plurality of ambulatory telemetry devices, each said device having means for mounting said device on a living being and means for transmitting RF signals from said each device including information on at least one physiological condition of the being and information uniquely identifying said each device;

means for receiving the signals of said each device including a separate receiver for each said telemetry device;

means operatively connected to the receivers which sequentially acquires the data from the receivers, extracts the information on the physiological condition from the received data, integrates it with the identifying information from the output signals and outputs said information on the condition and the identifying information in a given data format;

a data processing unit operatively connected to the means operatively connected to the receivers, which processes the information and dispatches the information on the physiological condition according to the identifying information;

means for dispatching from said each telemetry device said information on at least one physiological condition coupled with said information identifying said each telemetry device; and means for displaying said information from each said telemetry device on at least one physiological condition and information identifying said each telemetry device in a separate area on a video display.

21. An apparatus as claimed in claim 20, wherein each said telemetry device includes means for assigning values for said at least one physiological condition to parameters of messages, the messages being of different types and having a plurality of parameters forming a message parameter table, means for assembling said parameters into a digital message with a specific format for all messages including information about the type of message, and means for converting the digital message into a digital signal transmitted by said means for transmitting.

22. An apparatus as claimed in claim 21, wherein each message is transmitted twice to reduce error rate.

23. An apparatus as claimed in claim 20, having two receivers for each telemetry device tuned to a unique frequency for error reduction.

* * * * *